United States Patent [19]
Chern et al.

[11] Patent Number: 5,942,546
[45] Date of Patent: Aug. 24, 1999

[54] SULFONYL-N-HYDROXYGUANIDINE DERIVATIVES

[75] Inventors: Ji-Wang Chern, Taipei; Yu-Ling Leu, Hsien; Shan-Shue Wang, Tainan; Chin-Fen Lee, Keelung; Shih-Chung Hsu, Taipei Hsien, all of Taiwan

[73] Assignee: Development Center for Biotechnology, Taiwan

[21] Appl. No.: 08/975,286

[22] Filed: Nov. 20, 1997

[30] Foreign Application Priority Data

Apr. 10, 1997 [TW] Taiwan .................................. 86114520

[51] Int. Cl.$^6$ .......................... A61K 31/18; A61K 31/44; A61K 31/42; A61K 31/38; A61K 31/34; C07C 311/64; C07C 255/50; C07C 413/04; C07D 409/04; C07D 333/72; C07D 333/34; C07D 307/82; C07D 285/14

[52] U.S. Cl. .......................... 514/603; 514/336; 514/362; 514/378; 514/443; 514/445; 514/470; 514/524; 514/604; 546/280.4; 548/126; 548/247; 549/55; 549/65; 549/466; 558/413; 564/87; 564/89; 564/92

[58] Field of Search .................... 514/524, 603, 514/604, 336, 362, 378, 443, 445, 470; 564/87, 89, 92, 280.4; 548/126, 247; 549/55, 65, 466; 558/413

[56] References Cited

U.S. PATENT DOCUMENTS 5,234,955  8/1993  Ray et al. .................. 514/592
5,262,440  11/1993 Ehlhardt et al. .................. 514/392

OTHER PUBLICATIONS

Chern et al., "Synthesis and Cytotoxic Evaluation of Substituted Sulfonyl–N–hydroxyguanidine Derivatives as Potential Antitumor Agents," *J. Med. Chem.*, 40:2276–2286, 1997.

*Primary Examiner*—Michael G. Ambrose
*Attorney, Agent, or Firm*—Fish & Richardson P.C.

[57] ABSTRACT

A compound of the formula:

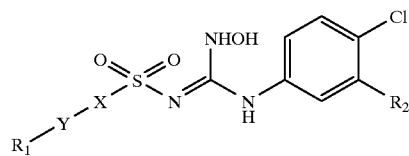

wherein X is arylene, heteroarylene, fused arylene, fused heteroarylene, or deleted; Y is sulfonyl, —O—, or deleted; $R_1$ is aryl, heteroaryl, fused aryl, or fused heteroaryl; $R_2$ is H, lower alkyl, lower alkoxy, halo, nitro, cyano, haloalkyl, hydroxyl, carboxyl, amido, amino, or aminoalkyl; or a salt thereof are disclosed. Also disclosed are a pharmaceutical composition which contains an excipient and an effective amount of a compound of the above formula and a method of treating cancer which involves the administration of an effective amount of such a compound to a patient in need thereof.

27 Claims, No Drawings

SULFONYL-N-HYDROXYGUANIDINE DERIVATIVES

BACKGROUND OF THE INVENTION

Sulfonylurea-containing compounds are known antitumor agents. See, e.g., U.S. Pat. No. 5,234,955 and U.S. Pat. No. 5,262,440. As these compounds have been found to accumulate in the mitochondria of cells, the mitochondria may be their target site of these compounds. Hydroxyguanidine-containing compounds have also been reported to possess potent antitumor activities. See Adamson, et al., Nature 1972, 236, 400 and Tai, et al. J. Med. Chem. 1984, 27, 236. The cellular target of hydroxyguanidine-containing compounds, however, is presumed to be ribonucleotide reductase.

SUMMARY OF THE INVENTION

The present invention [Chern, et al., J. Med. Chem. 1997, 40, 2276] features a series of sulfonyl-N-hydroxyguanidine derivatives.

An aspect of this invention relates to a compound of formula I:

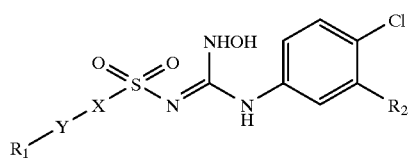

wherein X is arylene, heteroarylene, fused arylene, fused heteroarylene, or deleted; Y is sulfonyl or —O—; $R_1$ is aryl, heteroaryl, fused aryl, fused heteroaryl, or deleted; $R_2$ is H, lower alkyl, lower alkoxy, halo (e.g. fluoro, chloro, bromo, and iodo), nitro, cyano, haloalkyl, hydroxyl, carboxyl, amido, amino, or aminoalkyl; or a salt thereof. Such a salt can be formed between a compound of formula I and a counterion of the carboxyl group (e.g., sodium, ammonium, potassium, etc.) or the amino group (e.g., chloride, bromide, nitrate, etc.) of that compound.

One subset of the compounds covered by formula I are featured by that X and Y are deleted; $R_1$ is phenyl, substituted phenyl, benzothienyl, substituted benzothienyl, benzofuranyl, substituted benzofuranyl, benzothiadiazolyl, substituted benzothiadiazolyl, thienyl, substituted thienyl, in which each substituent of the substituted phenyl, substituted benzothienyl, substituted benzofuranyl, substituted benzothiadiazolyl, independently, is lower alkyl, lower alkoxy, halo, nitro, cyano, haloalkyl, hydroxyl, carboxyl, amido, amino, or aminoalkyl. The term "substituted" in this disclosure is defined as having one, two, or more substituents on the structure immediately following this term and the substituents can be identical or different. Preferable relative positions for the disubstituted structures include, but are not limited to meta-substituted phenyl and 3,5-disubstituted benzothienyl.

Another subset of the compounds covered by formula I are featured by that X is phenylene, substituted phenylene, thienyl, or substituted thienyl in which each substituent of the substituted phenylene and substituted thienyl, independently, is lower alkyl, lower alkoxy, halo, nitro, cyano, haloalkyl, hydroxyl, carboxyl, amido, amino, or aminoalkyl; $R_1$ is phenyl, substituted phenyl, benzothienyl, substituted benzothienyl, benzofuranyl, substituted benzofuranyl, benzothiadiazolyl, substituted benzothiadiazolyl, thienyl, substituted thienyl, in which each substituent of the substituted phenyl, substituted benzothienyl, substituted benzofuranyl, substituted benzothiadiazolyl, independently, is lower alkyl, lower alkoxy, halo, nitro, cyano, haloalkyl, hydroxyl, carboxyl, amido, amino, or aminoalkyl. Preferably, $R_2$ is H or halo. More preferably, X is substituted phenylene in which each substituent, independently, is halo, haloalkyl, nitro, amino, or aminoalkyl; and $R_1$ is phenyl, substituted phenyl, in which each substituent of said substituted phenyl, independently, is nitro or halo.

Another aspect of this invention relates to a pharmaceutical composition which contains an excipient and an effective amount of at least one of the sulfonyl-N-hydroxyguanidine derivatives of formula I, supra, or a salt thereof.

Also within the scope of this invention is a method of treating cancer (e.g., leukemia, hepatocellular cancer, cervical cancer, epidermoid oral cancer, and colon cancer). The method include the step of administering to a patient in need thereof an effective amount of at least a compound of the formula I, supra, or a salt thereof.

As used herein,. the terms "arylene" and "aryl" refer to $C_{6-10}$ bivalent and univalent hydrocarbon aromatic rings, respectively. Some examples of aryl and arylene include phenyl, phenylene, mesityl, tolyl, and xylyl. The substitution pattern of a bivalent arylene may be para, meta, or ortho. By "heteroarylene" or "heteroaryl" is meant $C_{3-9}$ bivalent or univalent heteroaromatic ring that contains one or more heteroatoms, e.g., nitrogen, oxygen, or sulfur. Typically, heteroaryls include, but are not limited to, pyridyl, pyrazinyl, pyrimidyl, furyl, pyrrolyl, thienyl, thiazolyl, oxazolyl, and imidazolyl. The terms "fused arylene" and "fused ayrl" are defined as $C_{8-12}$ bivalent and univalent polynuclear aromatic rings that contain two or more fused aromatic rings. Fused rings are rings that share a common carbon-carbon bond. Examples of fused arylenes and aryls include, but not limited to, naphthyl, biphenyl, indazolyl, phenanthryl, and anthracyl. The term "fused heteroarylene" or "fused heteroaryl" stands for a $C_{5-9}$ bivalent or univalent polynuclear heteroaromatic ring, which can contain one or more heteroatoms. Typical fused heteroaryls include, but are not restricted to, coumarinyl, indolyl, benzothienyl, benzofuranyl, benzothiadiazolyl and benzothiazolyl.

The term "lower alkyl" in this disclosure denotes a straight or branched hydrocarbon chain containing 1 to 8 carbon atoms, or cyclic hydrocarbon moieties containing 3 to 8 carbon atoms. These lower alkyl groups may also contain one or more double bond or triple bond. Examples of lower alkyl include, but are not limited to, methyl, ethyl, propyl, isopropyl, butyl, isobutyl, sec-butyl, tert-butyl, amyl, isopentyl, hexyl, isohexyl, heptyl, octyl, allyl, 2-butenyl, 2-pentenyl, 2-hexenyl, 2-butynyl, 2-pentynyl, 2-hexynyl, cyclopropyl, cyclopentyl, cyclohexyl, cycloheptyl, adamantyl, norbornyl, isobornyl, cyclohexylmethyl, 1- or 2-cyclohexylethyl, and 1-, 2-, or 3-cyclohexylpropyl. The term "lower alkoxy" represents the moiety —O-lower alkyl. Representatives of lower alkoxy include, but are not restricted to, methoxy, ethoxy, propoxy, isopropoxy, tert-butoxy, hexoxy, heptoxy, and octoxy. By the term "haloalkyl" or "aminoalkyl," on the other hand, is meant a lower alkyl group which is substituted with one or more halogen atoms or amino groups.

Set forth below are examples of compounds of this invention:

N-[(4-methylphenyl)sulfonyl]-N'-(4-chlorophenyl)-N"-hydroxyguanidine;

N-[(phenyl)sulfonyl]-N'-(4-chlorophenyl)-N''-hydroxyguanidine;
N-(4-chlorophenyl)-N'-[3,5-bis(trifluoromethyl)benzenesulfonyl]-N''-hydroxyguanidine;
N-(4-chlorophenyl)-N'-(5-chloro-3-methylbenzo[b]thiophene-2-sulfonyl)-N''-hydroxyguanidine;
N-(4-chlorophenyl)-N'-(benzo[b]thiophene-2-sulfonyl)-N''-hydroxyguanidine;
N-(4-chlorophenyl)-N'-(benzofuran-2-sulfonyl)-N''-hydroxyguanidine;
N-(4-chlorophenyl)-N'-[(benzo[2,1,3]thiadiazole-4-yl)sulfonyl]-N''-hydroxyguanidine;
N-(4-chlorophenyl)-N'-[2-(pyrid-2-yl)thiophene-5-sulfonyl]-N''-hydroxyguanidine;
N-(4-chlorophenyl)-N'-[5-(isoxazol-3-yl)thiophene-5-sulfonyl]-N''-hydroxyguanidine;
N-(4-chlorophenyl)-N'-(5-benzenesulfonylthiophene-2-sulfonyl)-N''-hydroxyguanidine;
N-(4-chlorophenyl)-N'-(4-benzenesulfonylthiophene-2-sulfonyl)-N''-hydroxyguanidine;
N-(4-chlorophenyl)-N'-[4-(3-chloro-2-cyanophenoxy)benzenesulfonyl]-N''-hydroxyguanidine;
N-(4-chlorophenyl)-N'-[4-(2-chloro-6-nitrophenoxy)benzenesulfonyl]-N''-hydroxyguanidine;
N-(4-chlorophenyl)-N'-[3,5-dichloro-4-(4-nitrophenoxy)benzenesulfonyl]-N''-hydroxyguanidine;
N-(4-chlorophenyl)-N'-[3,5-dichloro-4-(2-chloro-4-nitrophenoxy)benzenesulfonyl]-N''-hydroxyguanidine;
N-(4-chlorophenyl)-N'-[4-(n-butoxy)benzenesulfonyl]-N''-hydroxyguanidine;
N-(3,4-dichlorophenyl)-N'-(4-toluenesulfonyl)-N''-hydroxyguanidine;
N-(3,4-dichlorophenyl)-N'-(5-chloro-3-methylbenzo[b]thiophene-2-sulfonyl)-N'-hydroxyguanidine.

Other features and advantages of the present invention will be apparent from the following description of the preferred embodiments, and also from the appending claims.

DETAILED DESCRIPTION OF THE INVENTION

Sulfonyl-N-hydroxyguanidine derivatives of this invention can be prepared by the following synthetic reactions, A, B, C, and D.

As shown in reaction A below, reacting X—Y—$R_1$ substituted sulfonyl chloride of formula II with ammonia affords a sulfonamide derivative of formula III. Note that X, Y, $R_1$, as well as $R_2$, have been defined above.

Reaction A:

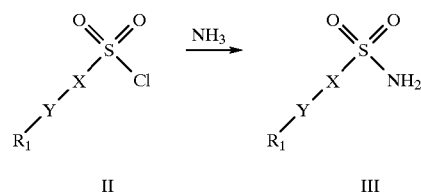

II       III

This resulting X—Y—$R_1$ substituted sulfonamide then reacts with a base to provide the corresponding reactive anion of formula IV, prior to contacting an isocyanate to obtain a compound of formula V (see reaction B below). A base has to be one that is strong enough to produce an sulfonamide anion. Some examples for such bases include sodium hydroxide, sodium hydride, and potassium hydroxide.

Reaction B:

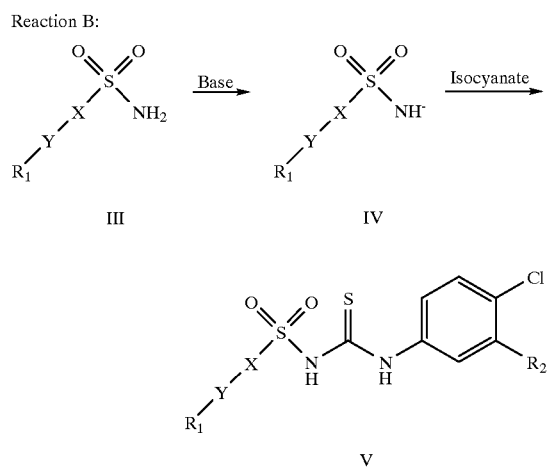

As shown in reaction C below, the resulting sulfonylthiourea derivative from the above reaction then reacts with methyl iodide in the presence of a base to form a methylated sulfonylthiourea compound of formula VI.

Reaction C:

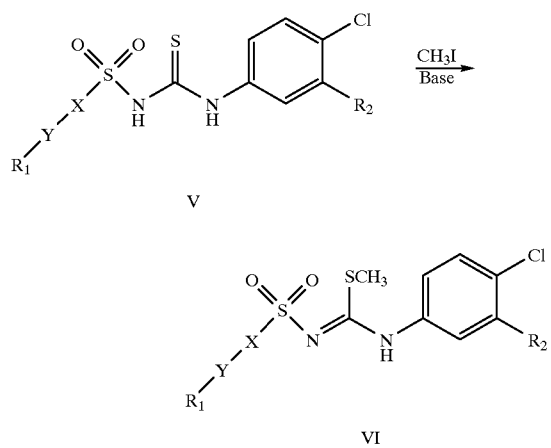

The final product of formula I is obtained via reaction D (illustrated below) by contacting methylated sulfonylthiourea with hydroxylamine.

Reaction D:

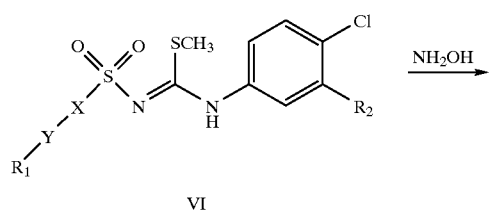

VI

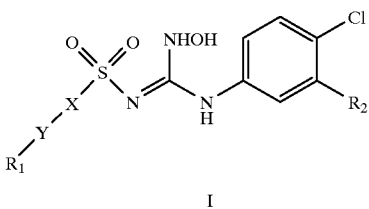

I

The solvent used in the above-mentioned reactions should be nonreactive. A preferred solvent for reaction A is dichloromethane. The reaction can be affected at a low temperature of, for example, −78° C.

When reaction B, i.e., the addition of sulfonamides of formula III to isothiocyanates, is complete, an acid, e.g., acetic acid, is added to neutralize the reaction mixture. Since isothiocyanates are easily decomposed in the presence of a base, the mole ratio between the sulfonamides and the base should be equal. Sodium hydroxide is one of the bases that can be employed in this reaction. The solvent used in this reaction should, again, be an inert one and acetone is a preferable choice.

In the next reaction, i.e., reaction C, a sulfonylthiourea of formula V reacts with a methyl iodide to afford a methylated pseudothiourea of formula VI. As sulfonylthioureas are susceptible to nucleophilic attack, compounds of formula V are directly treated with methyl iodide without isolation to afford the product.

In the last reaction, i.e., reaction D, a methylated sulfonylthiourea of formula VI reacts with hydroxylamine to afford a sulfonyl-N-hydroxylguanidine compound of formula I as a final product. Triethylamine or other bases with similar strength can be used and chloroform is a preferable solvent in this substitution reaction.

As set forth above, in addition to a pharmaceutical composition having an effective amount of a sulfonyl-N-hydroxyguanidine compound that contains an excipient, the present invention also provides a method of treating cancer by administering to a patient the just-described composition. As used in this disclosure, an effective amount of the sulfonyl-N-hydroxyguanidine compound is defined as the amount of the compound which, upon administration to a patient in need, inhibits growth of tumor cells, kills malignant cells, or reduces the size of the tumors, or otherwise confers a therapeutic effect on the treated patient. The effective amount to be administered to a patient is typically based on body surface area, patient weight, and patient condition. The interrelationship of dosages for animals and humans (based on milligrams per meter squared of body surface) is described by Freireich et al., Cancer Chemother. Rep. 1966, 50, 219. Body surface area may be approximately determined from height and weight of the patient. See, e.g., Scientific Tables, Geigy Pharmaceuticals, Ardley, N.Y., 1970, 537. An effective amount of a sulfonyl-N-hydroxyguanidine compound used to practive the invention can range from about 50 mg/kg to about 500 mg/kg, more preferably from about 100 mg/kg to about 400 mg/kg, and most preferably about 250 to about 350 mg/kg. Effective doses will also vary, as recognized by those skilled in the art, dependant on route of administration, excipient usage, and the possibility of co-usage with other therapeutic treatments including use of other anti-tumor agents and radiation therapy.

The pharmaceutical composition may be administered via the parenteral route, including subcutaneously, intraperitoneally, intramuscularly and intravenously. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds.

The sulfonyl-N-hydroxyguanidine compound can also be formulated into dosage forms for other routes of administration utilizing well-known methods. The pharmaceutical composition can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with the conventional procedure by compressing mixtures of the active sulfonyl-N-hydroxyguanidine compound and a solid carrier, and a lubricant. Examples of solid carriers include starch and sugar bentonite. The sulfonyl-N-hydroxyguanidine compound can also be administered in a form of a hard shell tablet or capsule containing, for example, lactose or mannitol as a binder and a conventional filler and a tableting agent.

The antitumor activity of sulfonyl-N-hydroxyguanidine compounds described above can be preliminarily evaluated using an in vitro assay, and then confirmed by in vivo testing. For example, the sulfonyl-N-hydroxyguanidine compounds can be evaluated by a microculture assay using 3-(4,5-dimethylthiazol-2-yl)2,5-diphenyltetrazolium bromide ("MTT") [Boyd, in "Principle of Practice of Oncology," Devita, Hellman, Rosenberg (eds.) Vol. 3, PPO Update, No. 10, 1989] for in vitro cytotoxicity. The MTT assay is based on the production of a dark blue formazan product by dehydrogenase in the mitochondria of live tumor cells after exposure to drug for 6 days [Alley, et al., Cancer Res. 1988, 48, 589]. Thus, only live cells are stained and can be measured at 570 nm. Antitumor cytotoxicity is reported as $IC_{50}$, effect drug dose at which cell growth is retarded to 50% of control culture of tumor cells.

Without further elaboration, it is believed that one skilled in the art can, based on the description herein, utilize the present invention to its fullest extent. The following specific examples are, therefore, to be construed as merely illustrative, and not limitative of the remainder of the disclosure in any way whatsoever. All publications recited herein, including patents, are hereby incorporated by reference in their entirety.

EXAMPLE 1

Preparation of N-[(4-methylphenyl)sulfonyl]-N'-(4-chlorophenyl)-N"-hydroxyguanidine To a solution containing 4-toluenesulfonyl chloride (10 g, 52.45 mmol) in dichloromethane (100 mL) at −78° C., liquid ammonia (20 mL) was added. After the mixture was stirred at −78° C. for 4 h, precipitates were removed by filtration and the filtrate was concentrated in vacuo to remove the solvent. The residue was then recrystallized from n-hexane/ethyl acetate (v/v=2:5) to give 7.77 g (85.7%) of 4-toluenesulfonamide.

1N sodium hydroxide solution (6 mL, 6 mmol) was added to a solution containing the 4-toluenesulfonamide (1 g, 5.85 mmol) in acetone (25 mL). After stirring at room temperature for 30 min, the 4-chlorophenyl isothiocyanate (1.0 mmol) was added. After refluxing for 4 h, the mixture was cooled to room temperature and neutralized with 1N acetic acid solution to pH 5. The mixture was allowed to stir at room temperature for 30 min before adding water (45 mL) to produce a white precipitate which was collected by filtration. After the solid was dried in the oven, it was recrystallized to give 0.45 g (22.6%) of N-[(4-methylphenyl) sulfonyl]-N'-(4-chlorophenyl)thiourea. To an aqueous solution (50 mL) of sulfonylthiourea (1.2 g, 3.67 mmol), 1N sodium hydroxide solution (4 mL) was added and stirred for 2 minutes, followed by addition of methyl iodide (4.04 mmol). The reaction mixture was stirred at room temperature for 20 minutes, and neutralized with 1N acetic acid (4 mL). The resulting mixture was extracted with chloroform to give 1.06 g (85%) of N-[(4-methylphenyl)sulfonyl]-N'-(4-chlorophenyl)-S-methylpseudothiourea. The S-methyl pseudourea (0.99 g, 2.8 mmol) was added to a stirred solution of hydroxylamine hydrochloride (8.4 mmol) and triethylamine (1.2 mL, 8.4 mmol) in chloroform (50 mL). The solution was refluxed for 48 h and the solvent was removed by evaporation to produce a solid residue. Ether (20 mL) was added to the residue and the white precipitate was collected by filtration. The solid was then heated with toluene and the undissolved solid was removed by filtration. The filtrate was again evaporated to obtain a solid which was subsequently recrystallized from methanol to yield the target compound (0.12 g, 12.7%); mp: 201–203° C.; MS m/z 294 (M$^+$–32); $^1$H NMR (300 MHz, DMSO-d$_6$) d 2.36 (s, 3H, CH$_3$), 7.31–7.36 (m, 4H, ArH), 7.45 (d, J=8.8 Hz, 2H, ArH), 7.71 (d, J=8.1 Hz, 2H, ArH), 9.40 (s, 1H, NH), 9.69 (br s, 2H, NH & OH); $^{13}$C NMR (100 MHz, DMSO-d$_6$) d 20.9, 124.7, 125.9, 128.2, 128.3, 129.1, 136.2, 140.6, 141.6, 154.0. Analysis for C$_{14}$H$_{14}$ClN$_3$O$_3$S (339.8): theory: C, 49.49; H, 4.15; N, 12.37. Found: C, 49.67; H, 4.16; N, 12.47.

EXAMPLE 2

Preparation of N-[(phenyl)sulfonyl]-N'-(4-chlorophenyl)-N"-hydroxyguanidine

N-[(phenyl)sulfonyl]-N'-(4-chlorophenyl)-N"-hydroxyguanidine was prepared starting from benzenesulfonyl chloride following the same procedure of Example 1. Analytical data of the above-described hydroxyguanidine derivative were given below.

Mp: 200–201° C.; MS m/z 343 (M$^+$+2); $^1$H NMR (300 MHz, DMSO-d$_6$) d 2.47 (s, 3H, SCH$_3$), 7.36 (d, J=8.7 Hz, 2H, ArH), 7.45 (d, J=8.7 Hz, 2H, ArH), 7.53–7.66 (m, 3H, ArH), 7.86 (d, J=8.4 Hz, 2H, ArH), 9.71 (s, 1H, NH); $^{13}$C NMR (100 MHz, DMSO-d$_6$) d 14.8, 126.2, 127.2, 128.7, 128.9, 131.3, 132.2, 136.3, 142.3, 166.3. Analysis for C$_{14}$H$_{13}$ClN$_2$O$_2$S$_2$ (340.85): theory: C, 49.33; H, 3.84; N, 8.22. Found: C, 49.20; H, 3.84; N, 8.15.

EXAMPLE 3

Preparation of N-(4-chlorophenyl)-N'-[3,5-bis(trifluoromethyl)benzenesulfonyl]-N"-hydroxyguanidine 3,5-bis(trifluoro-methyl)benzenesulfonamide (formula III) was obtained following the procedure as described in the first paragraph of Example 1 utilizing 3,5-bis(trifluoromethyl)-benzenesulfonyl chloride as starting material.

1N sodium hydroxide solution (1.0 mL) was added to a solution the containing the sulfonamide of formula III (3.4 mmol) in acetone (25 mL). A solution of the 4-chlorophenyl isothiocyanates (3.6 mmol) in acetone (25 mL) was added. After stirring at room temperature for 4 h, methyl iodide (6.8 mmol) was added to the filtrate. The reaction mixture was stirred for 30 min before neutralized with 1N hydrochloric acid. The solid was collected and recrystallized from methanol to afford the S-methyl pseudothiourea of formula V.

Hydroxylamine hydrochloride (0.44 g, 6.3 mmol) and triethylamine (6.3 mmol) were dissolved in acetonitrile (50 mL) and stirred for a half hour. The S-methyl pseudourea from the last step (1.5 g, 3.15 mmol) was then added to the mixture and stirred in room temperature for further 5 days. The product was purified over silica gel column to obtain the 318 mg (22%) of the final product. Mp: 192° C.; MS m/z 461.4 (M$^+$); $^1$H NMR (300 MHz, DMSO-d$_6$) d 7.30–7.40 (m, 4H, ArH), 8.32 (s, 2H, ArH), 8.37 (s, 1H, ArH), 9.61 (s, 1H, NH), 10.01 (s, 1H, NH), 10.27 (s, 1H, OH); $^{13}$C NMR (75 MHz, DMSO-d$_6$) d 123.1 (q, J=272 Hz, CF$_3$), 125.7, 126.0, 126.9, 128.6, 129.4, 131.3 (q, J=33 Hz, CCF$_3$), 136.3, 146.8, 154.2. Analysis for C$_{15}$H$_{10}$F$_6$ClN$_3$O$_3$S (461.77): theory: C, 39.02; H, 2.18; N, 9.10. Found: C, 39.76; H, 2.44; N, 8.89.

EXAMPLE 4

Preparation of N-(4-chlorophenyl)-N'-(5-chloro-3-methylbenzo[b]thiophene-2-sulfonyl)-N"-hydroxyguanidine N-(4-chlorophenyl)-N'-(5-chloro-3-methylbenzo[b]thiophene-2-sulfonyl)-N"-hydroxyguanidine was prepared starting from 5-chloro-3-methylbenzo[b]thiophene-2-sulfonyl chloride following the same procedure of Example 1. The crude product was purified over silica gel and recrystallized from methanol. Analytical data of the above-described hydroxyguanidine derivative were given below.

Mp: 245–247° C.; MS m/z 413 (M$^+$–17); $^1$H NMR (300 MHz, DMSO-d$_6$) d 2.52 (s, 3H, CH$_3$), 7.35 (d, J=8.9 Hz, 2H, ArH), 7.45 (d, J=8.9 Hz, 2H, ArH), 7.52 (dd, J=8.7 Hz, J=1.9 Hz, 1H, ArH), 7.96 (d, J=1.9 Hz, 1H, ArH), 8.05 (d, J=8.7 Hz, 1H, ArH), 9.60 (s, 1H, NH), 9.97 (s, 2H, NH & OH); $^{13}$C NMR (75 MHz, DMSO-d$_6$) d 12.3, 123.3, 124.9, 125.6, 127.1, 128.6, 129.2, 130.5, 133.4, 136.7, 141.4, 154.5. HRMS for C$_{16}$H$_{13}$O$_3$S$_2$N$_3$Cl$_2$: theory: 428.9775. Found: 428.9774.

EXAMPLE 5

Preparation of N-(4-chlorophenyl)-N'-(benzo[b]thiophene-2-sulfonyl)-N"-hydroxyguanidine To a solution of benzothiophene (2.23 g, 16.6 mmol) in THF (40 mL) at room temperature was added 1.6 M n-butyllithium in hexane (10.4 mL, 16.6 mmol). The reaction mixture was refluxed for 4 h and then evaporated to dryness in vacuo. To the residue was added water (100 mL), sodium acetate (10.89 g, 0.13 mol) and hydroxylamine-O-sulfonic acid (6.26 g, 0.05 mol). The mixture was allowed to stir at room temperature for 8 h and was then ether extracted (75 mL×2). The organic layer was extracted with 1N sodium hydroxide (50 mL×3). The aqueous layer was collected and neutralized with 1N hydrochloride solution followed by extraction with dichloromethane (50 mL×3). The organic layer was collected and dried over anhydrous sodium sulfate. Concentration in vacuo yielded a yellow solid which was recrystallized from methanol and water (1:1) to give benzo[b]thiophene-2-sulfonamide (0.28 g, 7.8%).

N-(4-chlorophenyl)-N'-(benzo[b]thiophene-2-sulfonyl)-N"-hydroxyguanidine was obtained in accordance with the procedure as described in the second and third paragraphs of Example 3 utilizing benzo[b]thiophene-2-sulfonamide as starting material. Analytical data of this above-described hydroxyguanidine derivative were as follows. Mp: 264–266° C.; MS m/z 381 (M$^+$); $^1$H NMR (300 MHz, DMSO-d$_6$) d 7.36–7.39 (m, 2H, ArH), 7.45–7.50 (m, 4H, ArH), 7.96–8.05 (m, 2H, ArH), 9.57 (s, 1H, NH), 9.99 (s, 2H, OH & NH); $^{13}$C NMR (75 MHz, DMSO-d$_6$) d 123.3, 123.8, 125.6, 125.7, 125.8, 127.1, 128.6, 129.1, 136.4, 137.9, 140.8, 145.2, 154.4. Analysis for C$_{15}$H$_{12}$ClN$_3$O$_3$S$_2$ (381.86): theory: C, 47.18; H, 3.17; N, 11.00. Found: C, 47.10; H, 3.21; N, 10.76.

EXAMPLE 6

Preparation of N-(4-chlorophenyl)-N'-(benzofuran-2-sulfonyl)-N"-hydroxyguanidine N-(4-chlorophenyl)-N'-(benzofuran-2-sulfonyl)-N"-hydroxyguanidine was prepared starting from benzofuran following the same procedure of Example 5. The crude product was purified over silica gel and recrystallized from methanol. Analytical data of this hydroxyguanidine derivative were as follows. Mp: 207–229° C.; MS m/z 366 (M$^+$); $^1$H NMR (300 MHz, DMSO-d$_6$) d 7.33–7.50 (m, 7H, ArH), 7.69 (d, J=8.2 Hz, 1H, ArH), 7.77 (d, J=7.7 Hz, 1H, ArH), 9.62 (s, 1H, NH), 10.09 (s, 2H, NH & OH); $^{13}$C NMR (75 MHz, DMSO-d$_6$) d 106.6, 109.4, 112.3, 123.3, 124.4, 125.6, 126.5, 127.4, 128.6, 129.1, 136.4, 154.0, 154.2. Analysis for C$_{15}$H$_{12}$ClN$_3$O$_4$S (365.80): theory: C, 49.25; H, 3.31; N, 11.49. Found: C, 49.24; H, 3.15; N, 11.56.

EXAMPLE 7

Preparation of N-(4-chloro-phenyl)-N'-[(benzo-[2,1,3]-thiadiazole-4-yl)sulfonyl]-N"-hydroxyguanidine N-(4-chlorophenyl)-N'-[(benzo[2,1,3]thiadiazole-4-yl)sulfonyl]-N"-hydroxyguanidine was prepared from benzo[2,1,3]-thiadiazole-4-sulfonyl chloride following the same procedure of Example 1. The crude product was purified over silica gel and recrystallized from methanol. Analytical data of this hydroxyguanidine derivative were given below. Mp: 217–218° C.; MS m/z 366.5 (M$^+$–17); $^1$H NMR (300 MHz, DMSO-d$_6$) d 7.24 (d, J=8.9 Hz, 2H, ArH), 7.43 (d, J=8.9 Hz, 2H, ArH), 7.83 (dd, J=8.8 Hz, 7.1 Hz, 1H, ArH), 8.22 (dd, J=7.1 Hz, 1.1 Hz, 1H, ArH), 8.31 (dd, J=8.8 Hz, 1.1 Hz, 1H, ArH), 9.47 (s, 1H, NH), 9.95 (s, 2H, NH & OH); $^{13}$C NMR (75 MHz, DMSO-d$_6$) d 125.0, 125.5, 128.4, 128.6, 129.2, 129.4, 135.1, 136.5, 154.6, 155.5, 158.3. Analysis for C$_{13}$H$_{10}$ClN$_5$O$_3$S$_2$ (383.8): theory: C, 40.68; H, 2.63; N, 18.25. Found: C, 40.86; H, 2.38; N, 18.15.

EXAMPLE 8

Preparation of N-(4-chlorophenyl)-N'-[2-(pyrid-2-yl)thiophene-5-sulfonyl]-N"-hydroxy-guanidine N-(4-chlorophenyl)-N'-[2-(pyrid-2-yl)thiophene-5-sulfonyl]-N"-hydroxy-guanidine was prepared starting from 2-(pyrid-2-yl)thiophene-5-sulfonyl chloride following the same procedure of Example 3. The crude product was purified over silica gel and recrystallized from acetonitrile. Analytical data of this hydroxyguanidine derivative were given below. Mp: 210° C.; MS m/z 411 (M$^+$+1); $^1$H NMR (300 MHz, DMSO-d$_6$) d 7.33–7.39 (m, 3H, ArH), 7.47 (d, J=8.9 Hz, 2H, ArH), 7.61 (d, J=4.0 Hz, 1H, thiophene-H), 7.77 (d, J=4.0 Hz, 1H, thiophene-H), 7.88 (td, J=7.8 Hz, J=1.6 Hz, 1H, ArH), 8.00 (d, J=7.8 Hz, 1H, ArH), 9.55 (s, 1H, NH), 9.97 (s, 2H, NH & OH); $^{13}$C NMR (75 MHz, DMSO-d$_6$) d 119.6, 123.9, 124.7, 125.4, 128.6, 129.0, 131.3, 136.5, 137.8, 146.1, 148.9, 150.0, 151.1, 154.3. Analysis for C$_{16}$H$_{13}$ClN$_4$O$_3$S$_2$ (408.89): theory: C, 47.00; H, 3.20; N, 13.70. Found: C, 47.25; H, 3.00; N, 13.60.

EXAMPLE 9

Preparation of N-(4-chlorophenyl)-N'-[5-(isoxazol-3-yl)thiophene-5-sulfonyl]-N"-hydroxyguanidine N-(4-chlorophenyl)-N'-[5-(isoxazol-3-yl)thiophene-5-sulfonyl]-N"-hydroxyguanidine was prepared starting from 5-(isoxazol-3-yl)thiophene-5-sulfonyl chloride following the same procedure of Example 1. The crude product was purified over silica gel and recrystallized from benzene. Analytical data of this hydroxyguanidine derivative were given below. Mp: 184° C.; MS m/z 396 (M$^+$–3); $^1$H NMR (300 MHz, DMSO-d$_6$) d 7.05 (d, J=1.8 Hz, 1H, thiophene-H), 7.41 (q, J=9.0 Hz, 4H, ArH), 7.68 (s, 2H, ArH), 7.72 (d, J=1.8 Hz, thiophene-H), 9.60 (s, 1H, NH), 10.05 (s, 2H, NH & OH). Analysis for C$_{14}$H$_{11}$ClN$_4$O$_4$S$_2$ (399.13): theory: C, 42.13; H, 2.78; N, 14.04. Found: C, 42.20; H, 2.75; N, 14.10.

EXAMPLE 10

Preparation of N-(4-chlorophenyl)-N'-(5-benzenesulfonylthiophene-2-sulfonyl)-N"-hydroxyguanidine N-(4-chlorophenyl)-N'-(5-benzenesulfonylthiophene-2-sulfonyl)-N"-hydroxyguanidine was prepared starting from 2-benzenesulfonylthiophene-5-sulfonyl chloride following the same procedure of Example 1. The crude product was purified over silica gel. Analytical data of this hydroxyguanidine derivative were as follows. Mp: 195–196° C.; MS m/z 413 (M$^+$–59); $^1$H NMR (300 MHz, DMSO-d$_6$) d 7.32 (s, 4H, ArH), 7.59 (d, J=4.0 Hz, 1H, thiophene-H), 7.65–7.78 (m, 3H, ArH), 8.03 (d, J=7.1 Hz, 2H, ArH), 9.65 (s, 1H, NH), 10.05 (s, 1H, OH), 10.20 (s, 1H, NH); $^{13}$C NMR (75 MHz, DMSO-d$_6$) d 125.6, 125.9, 127.6, 128.6, 129.4, 130.2, 130.4, 134.0, 134.8, 134.8, 136.1, 141.0, 145.2, 153.4, 154.2. Analysis for C$_{17}$H$_{14}$ClN$_3$O$_5$S$_3$ (471.97): theory: C, 43.26; H, 2.99; N, 8.90. Found: C, 43.48; H, 2.93; N, 8.67.

EXAMPLE 11

Preparation of N-(4-chlorophenyl)-N'-(4-benzenesulfonylthiophene-2-sulfonyl)-N"-hydroxyguanidine N-(4-chlorophenyl)-N'-(4-benzenesulfonylthiophene-2-sulfonyl)-N"-hydroxyguanidine was prepared starting from 4-benzene-sulfonylthiophene-2-sulfonyl chloride following the same procedure of Example 1. The crude product was purified over silica gel. Analytical data of this hydroxyguanidine derivative were given as follows. Mp: 195° C.; MS m/z 413 (M$^+$–59); $^1$H NMR (300 MHz, DMSO-d$_6$) d 7.34 (s, 4H, ArH), 7.64–7.75 (m, 3H, ArH), 7.81 (d, J=1.6 Hz, 1H, thiophene-H), 8.01 (d, J=7.4 Hz, 2H, ArH), 8.63 (d, J=1.6 Hz, 1H, thiophene-H), 9.59 (s, 1H, NH), 10.04 (s, 1H, OH), 10.15 (s, 1H, NH); $^{13}$C NMR (75 MHz, DMSO-d$_6$) d 106.2, 125.8, 127.0, 127.7, 128.6, 129.3, 130.3, 134.5, 136.2, 136.8, 140.8, 140.9, 154.1. Analysis for C$_{17}$H$_{14}$ClN$_3$O$_5$S$_3$ (471.97): theory: C, 43.26; H, 2.99; N, 8.90. Found: C, 43.26; H, 2.78; N, 8.73.

EXAMPLE 12

Preparation of N-(4-chlorophenyl)-N'-[4-(3-chloro-2-cyanophenoxy)benzenesulfonyl]-N"-hydroxyguanidine N-(4-chlorophenyl)-N'-[4-(3-chloro-2-cyanophenoxy)benzenesulfonyl]-N"-hydroxyguanidine was prepared starting 4-(3-chloro-2-cyanophenoxy)benzenesulfonyl chloride following the same procedure of Example 3. The crude product was purified over silica gel and recrystallized from methanol. Analytical data of this hydroxyguanidine derivative were given below. Mp: 199° C.; MS m/z 418 (M$^+$–59); $^1$H NMR (300 MHz, DMSO-d$_6$) d 8.11 (d, J=8.3 Hz, 1H, ArH), 7.30–7.37 (m, 4H, ArH), 7.45 (d, J=8.9 Hz, 2H, ArH), 7.56 (d, J=8.2 Hz, 1H, ArH), 7.72 (t, J=8.3 Hz, 1H, ArH), 7.90 (d, J=8.7 Hz, 2H, ArH), 9.47 (s, 1H, NH), 9.88 (s, 2H, NH & OH); $^{13}$C NMR (75 MHz, DMSO-d$_6$) d 104.8, 113.0, 117.5, 119.0, 124.8, 125.2, 128.2, 128.4, 128.5, 136.0, 136.2, 136.5, 140.0, 154.0, 157.1, 159.0. Analysis for C$_{20}$H$_{14}$Cl$_2$N$_4$O$_4$S (477.33): theory: C, 50.33; H, 2.96; N, 11.74. Found: C, 50.30; H, 2.96; N, 11.87.

EXAMPLE 13

Preparation of N-(4-chlorophenyl)-N'-[4-(2-chloro-6-nitrophenoxy)benzenesulfonyl]-N"-hydroxyguanidine N-(4-chlorophenyl)-N'-[4-(2-chloro-6-nitrophenoxy)benzenesulfonyl]-N"-hydroxyguanidine was prepared starting 4-(2-chloro-6-nitrophenoxy)benzenesulfonyl chloride following the same procedure of Example 3. The crude product was purified over silica gel and recrystallized from acetonitrile. Analytical data of this hydroxyguanidine derivative were as follows. Mp: 199° C.; MS m/z 364.5 (M$^+$–132); $^1$H NMR (300 MHz, DMSO-d$_6$) d 7.03 (d, J=8.8 Hz, 2H, ArH), 7.33 (d, J=8.9 Hz, 2H, ArH), 7.43 (d, J=8.9 Hz, 2H, ArH), 7.63 (t, J=8.2 Hz, 1H, ArH), 7.81 (d, J=8.8 Hz, 2H, ArH), 8.08 (dd, J=8.2 Hz, J=1.5 Hz, 1H, ArH), 8.18 (dd, J=8.2 Hz, J=1.5 Hz, 1H, ArH), 9.46 (s, 1H, NH), 9.85 (br s, 2H, NH & OH); $^{13}$C NMR (75 MHz, DMSO-d$_6$) d 115.5, 125.2, 125.4, 128.3, 128.6, 128.7, 128.8, 129.6, 136.4, 136.6, 138.3, 142.7, 144.7, 154.3, 158.9. Analysis for C$_{19}$H$_{14}$Cl$_2$N$_4$O$_6$S (497.3): theory: C, 45.89; H, 2.84; N, 11.27. Found: C, 45.82; H, 2.86; N, 11.13.

EXAMPLE 14

Preparation of N-(4-chlorophenyl)-N'-[3,5-dichloro-4-(4-nitrophenoxy)benzenesulfonyl]-N"-hydroxyguanidine N-(4-chlorophenyl)-N'-[3,5-dichloro-4-(4-nitrophenoxy)benzenesulfonyl]-N"-hydroxyguanidine was prepared starting 3,5-dichloro-4-(4-nitrophenoxy)-benzenesulfonyl chloride following the same procedure of Example 3. The crude product was purified over silica gel and recrystallized from methanol. Analytical data of this above-titled hydroxyguanidine derivative were given below. Mp: 212° C.; MS m/z 473.8 (M$^+$–58); $^1$H NMR (300 MHz, DMSO-d$_6$) d 7.16 (d, J =9.2 Hz, 2H, ArH), 7.38 (d, J=8.9 Hz, 2H, ArH), 7.46 (d, J=8.9 Hz, 2H, ArH), 8.06 (s, 2H, ArH), 8.26 (d, J=9.2 Hz, 2H, ArH), 9.61 (s, 1H, NH), 10.06 (s, 1H, OH), 10.16 (s, 1H, NH); $^{13}$C NMR (75 MHz, DMSO-d$_6$) d 115.7, 123.6, 125.4, 126.4, 127.4, 128.3, 128.8, 136.0, 143.0, 143.3, 147.3, 153.8, 160.3. Analysis for C$_{19}$H$_{13}$Cl$_3$N$_4$O$_6$S (531.76): theory: C, 42.92; H, 2.46; N, 10.54. Found: C, 43.30; H, 2.44; N, 10.49.

EXAMPLE 15

Preparation of N-(4-chlorophenyl)-N'-[3,5-dichloro-4-(2-chloro-4-nitrophenoxy)benzenesulfonyl]-N"-hydroxyguanidine N-(4-chlorophenyl)-N'-[3,5-dichloro-4-(2-chloro-4-nitrophenoxy)benzenesulfonyl]-N"-hydroxyguanidine was prepared starting 4-(2-chloro-4-nitrophenoxy)-3,5-dichlorobenzenesulfonyl chloride following the same procedure of Example 3. The crude product was purified over silica gel and recrystallized from chloroform. Analytical data of this above-titled hydroxyguanidine derivative were given below. Mp: 180° C.; MS m/z 552 (M$^+$+4); $^1$H NMR (300 MHz, DMSO-d$_6$) d 6.96 (d, J=9.2 Hz, 1H, ArH), 7.37 (d, J=8.9 Hz, 2H, ArH), 7.46 (d, J=8.9 Hz, 2H, ArH), 8.08 (s, 2H, ArH), 8.11 (dd, J=9.2 Hz, J=2.7 Hz, 1H, ArH), 8.53 (d, J=2.7 Hz, 1H, ArH), 9.61 (s, 1H, NH), 10.08 (br s, 2H, NH & OH); $^{13}$C NMR (75 MHz, DMSO-d$_6$) d 115.3, 122.4, 125.0, 125.8, 126.9, 127.9, 128.7, 128.9, 129.2, 136.4, 143.6, 144.0, 147.5, 154.1, 156.1. Analysis for C$_{19}$H$_{12}$Cl$_4$N$_4$O$_6$S.H$_2$O (584.22): theory: C, 39.06; H, 2.42; N, 9.59. Found: C, 39.06; H, 2.29; N, 9.48.

EXAMPLE 16

Preparation of N-(4-chlorophenyl)-N'-[4-(n-butoxy)-benzenesulfonyl]-N"-hydroxyguanidine N-(4-chlorophenyl)-N'-[4-(n-butoxy)benzenesulfonyl]-N"-hydroxyguanidine was prepared starting 4-(n-butoxy)benzenesulfonyl chloride following the same procedure of Example 3. The crude product was purified over silica gel and recrystallized from methanol. Analytical data of this hydroxyguanidine derivative were given below. Mp: 175–176° C.; MS m/z 381 (M$^+$–16); $^1$H NMR (300 MHz, DMSO-d$_6$) d 0.93 (t, J=7.3 Hz, 3H, CH$_3$), 1.37–1.49 (m, 2H, CH$_2$), 1.65–1.75 (m, 2H, CH$_2$), 4.02 (t, J=6.4 Hz, 2H, OCH$_2$), 7.03 (d, J=8.9 Hz, 2H, ArH), 7.35 (d, J=8.9 Hz, 2H, ArH), 7.47 (d, J=8.9 Hz, 2H, ArH), 7.74 (d, J 8.9 Hz, 2H, ArH), 9.38 (s, 1H, NH), 9.77 (s, 2H, NH & OH); $^{13}$C NMR (75 MHz, DMSO-d$_6$) d 14.0, 19.0, 31.0, 67.9, 114.6, 125.0, 128.4, 128.6, 135.6, 136.7, 154.3, 161.4, 162.5. Analysis C$_{17}$H$_{20}$ClN$_3$O$_4$S (397.88): theory: C, 51.32; H, 5.07; N, 10.56. Found: C, 51.41; H, 5.02; N, 10.26.

EXAMPLE 17

Preparation of N-(3,4-dichlorophenyl)-N'-(4-toluenesulfonyl)-N"-hydroxyguanidine N-(3,4-dichlorophenyl)-N'-(4-toluenesulfonyl)-N"-hydroxyguanidine was prepared starting 4-toluenesulfonyl chloride following the same procedure of Example 1, except that 4-chlorophenyl isothiocyanate of the second reaction was replaced by 3,4-dichlorophenyl isothiocyanate. The crude product was purified over silica gel and recrystallized from methanol. Analytical data of the above-titled hydroxyguanidine derivative were given below. Mp: 195° C.; MS m/z 375 (M$^+$); $^1$H NMR (300 MHz, DMSO-d$_6$) d 2.36 (s, 3H, CH$_3$), 7.34 (d, J=8.1 Hz, 2H, ArH), 7.46–7.56 (m, 2H, ArH), 7.71–7.75 (m, 3H, ArH), 9.51 (s, 1H, NH), 9.92 (s, 2H, NH & OH); $^{13}$C NMR (75 MHz, DMSO-d$_6$) d 20.9, 122.7, 124.0, 125.8, 129.2, 130.1, 130.4, 137.6, 140.5, 141.7, 153.4. Analysis C$_{14}$H$_{13}$Cl$_2$N$_3$O$_3$S (374.25): theory: C, 44.93; H, 3.50; N, 11.23. Found: C, 44.80; H, 3.50; N, 11.08.

EXAMPLE 18

Preparation of N-(3,4-dichlorophenyl)-N'-(5-chloro-3-methylbenzo[b]thiophene-2-sulfonyl)-N'-hydroxyguanidine N-(3,4-dichlorophenyl)-N'-(5-chloro-3-methylbenzo[b]thiophene-2-sulfonyl)-N'-hydroxyguanidine was prepared starting 5-chloro-3-methylbenzo[b]thiophene-2-sulfonyl chloride following the same procedure of Example 4, except that 4-chlorophenyl isothiocyanate of the second reaction was replaced by 3,4-dichlorophenyl isothiocyanate. The crude product was purified over silica gel and recrystallized from acetonitrile and methanol and ethyl acetate. Analytical data of this above-titled hydroxyguanidine derivative were given below. Mp: 232–233° C.; MS m/z 466 (M$^+$+1); $^1$H NMR (300 MHz, DMSO-d$_6$) d 2.56 (s, 3H, CH$_3$), 7.45 (dd, J=8.8 Hz, J=2.4 Hz, 1H, ArH), 7.51–7.57 (m, 2H, ArH), 7.73 (d, J=2.4 Hz, 1H, ArH), 7.97 (d, J=2.0 Hz, 1H, ArH), 8.05 (d, J=8.6 Hz, 1H, ArH), 9.69 (s, 1H, NH), 10.10 (br s, 2H, NH & OH); $^{13}$C NMR (75 MHz, DMSO-d$_6$) d 12.3, 100.7, 106.6, 123.4, 123.5, 124.8, 124.9, 127.2, 130.5, 130.6, 133.4, 136.7, 137.7, 141.4, 153.8. Analysis C$_{16}$H$_{12}$Cl$_3$N$_3$O$_3$S$_2$ (464.78): theory: C, 41.35; H, 2.60; N, 9.04. Found: C, 41.32; H, 2.49; N, 8.76.

OTHER EMBODIMENTS

From the above description, one skilled in the art can easily ascertain the essential characteristics of the present invention, and without departing from the spirit and scope thereof, can make carious changes and modifications of the invention to adapt it to various usages and conditions. Thus, other embodiments are also within the claims.

What is claimed is:

1. A compound of the formula

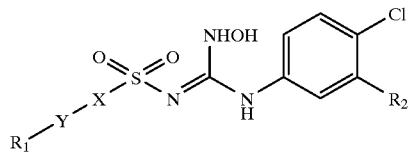

wherein
   X is arylene, heteroarylene, fused arylene, fused heteroarylene, or deleted;
   Y is sulfonyl, —O—, or deleted;
   R$_1$ is aryl, heteroaryl, fused aryl, or fused heteroaryl; and
   R$_2$ is H, lower alkyl, lower alkoxy, halo, nitro, cyano, haloalkyl, hydroxyl, carboxyl, amido, amino, or aminoalkyl;
or a salt thereof.

2. The compound of claim 1, wherein
   X and Y are deleted; and
   R$_1$ is phenyl, substituted phenyl, benzothienyl, substituted benzothienyl, benzofuranyl, substituted benzofuranyl, benzothiadiazolyl, substituted benzothiadiazolyl, thienyl, substituted thienyl, in which each substituent of said substituted phenyl, substituted benzothienyl, substituted benzofuranyl, and substituted benzothiadiazolyl, independently, is lower alkyl, lower alkoxy, halo, nitro, cyano, haloalkyl, hydroxyl, carboxyl, amido, amino, or aminoalkyl;
or a salt thereof.

3. The compound of claim 1, wherein
   X is phenylene, substituted phenylene, thienyl, or substituted thienyl in which each substituent of said substituted phenylene and substituted thienyl, independently, is lower alkyl, lower alkoxy, halo, nitro, cyano, haloalkyl, hydroxyl, carboxyl, amido, amino, or aminoalkyl; and
   R$_1$ is phenyl, substituted phenyl, benzothienyl, substituted benzothienyl, benzofuranyl, substituted benzofuranyl, benzothiadiazolyl, substituted benzothiadiazolyl, thienyl, substituted thienyl, in which each substituent of said substituted phenyl, substituted benzothienyl, substituted benzofuranyl, substituted benzothiadiazolyl, independently, is lower alkyl, lower alkoxy, halo, nitro, cyano, haloalkyl, hydroxyl, carboxyl, amido, amino, or aminoalkyl;
or a salt thereof.

4. The compound of claim 3, wherein
   X is thienyl or substituted thienyl in which each substituent of said substituted thienyl, independently, is lower alkyl, lower alkoxy, halo, nitro, cyano, haloalkyl, hydroxyl, carboxyl, amido, amino, or aminoalkyl;
   Y is sulfonyl or deleted;
or a salt thereof.

5. The compound of claim 3, wherein
   X is phenylene or substituted phenylene in which each substituent of said substituted phenylene is, independently, lower alkyl, lower alkoxy, halo, nitro, cyano, haloalkyl, hydroxyl, carboxyl, amido, amino, or aminoalkyl; and
   Y is —O—;
or a salt thereof.

6. The compound of claim 5, wherein R$_2$ is H or halo; or a salt thereof.

7. The compound of claim 6, wherein
   X is phenylene or substituted phenylene in which each substituent of said substituted phenylene is, independently, halo, haloalkyl, nitro, amino, or aminoalkyl; and
   R$_1$ is phenyl or substituted phenyl in which each substituent of said phenyl, independently, is nitro or halo;
or a salt thereof.

8. The compound of claim 7, wherein X is 3,5-dichlorophenyl; Y is —O—; and R$_1$ is 4-nitrophenyl and R$_2$ is H.

9. The compound of claim 7, wherein X is 3,5-dichlorophenyl; Y is —O—; and R$_1$ is 2-chloro-4-nitrophenyl and R$_2$ is H.

10. A pharmaceutical composition, comprising an excipient and an effective amount of a compound of the formula:

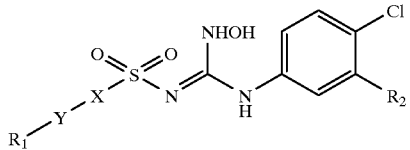

wherein
   X is arylene, heteroarylene, fused arylene, fused heteroarylene, or deleted;
   Y is sulfonyl, —O—, or deleted;
   R$_1$ is aryl, heteroaryl, fused aryl, or fused heteroaryl; and
   R$_2$ is H, lower alkyl, lower alkoxy, halo, nitro, cyano, haloalkyl, hydroxyl, carboxyl, amido, amino, or aminoalkyl;
or a salt thereof.

11. The composition of claim 10, wherein
   X and Y are deleted; and
   R$_1$ is phenyl, substituted phenyl, benzothienyl, substituted benzothienyl, benzofuranyl, substituted benzofuranyl, benzothiadiazolyl, substituted benzothiadiazolyl, thienyl, substituted thienyl, in which each substituent of said substituted phenyl, substituted benzothienyl, substituted benzofuranyl, substituted benzothiadiazolyl, independently, is lower alkyl, lower alkoxy, halo, nitro, cyano, haloalkyl, hydroxyl, carboxyl, amido, amino, or aminoalkyl.

12. The composition of claim 10, wherein

X is phenylene, substituted phenylene, thienyl, or substituted thienyl in which each substituent of said substituted phenylene and substituted thienyl, independently, is lower alkyl, lower alkoxy, halo, nitro, cyano, haloalkyl, hydroxyl, carboxyl, amido, amino, or aminoalkyl; and $R_1$ is phenyl, substituted phenyl, benzothienyl, substituted benzothienyl, benzofuranyl, substituted benzofuranyl, benzothiadiazolyl, substituted benzothiadiazolyl, thienyl, substituted thienyl, in which each substituent of said substituted phenyl, substituted benzothienyl, substituted benzofuranyl, substituted benzothiadiazolyl, independently, is lower alkyl, lower alkoxy, halo, nitro, cyano, haloalkyl, hydroxyl, carboxyl, amido, amino, or aminoalkyl.

13. The composition of claim 12, wherein

X is thienyl or substituted thienyl in which each substituent of said substituted thienyl, independently, is lower alkyl, lower alkoxy, halo, nitro, cyano, haloalkyl, hydroxyl, carboxyl, amido, amino, or aminoalkyl; and Y is sulfonyl or deleted.

14. The composition of claim 12, wherein

X is phenylene or substituted phenylene in which each substituent of said substituted phenylene is, independently, lower alkyl, lower alkoxy, halo, nitro, cyano, haloalkyl, hydroxyl, carboxyl, amido, amino, or aminoalkyl; and Y is —O—.

15. The composition of claim 14, wherein $R_2$ is H or halo.

16. The composition of claim 15, wherein

X is phenylene or substituted phenylene in which each substituent of said substituted phenylene is, independently, halo, haloalkyl, nitro, amino, or aminoalkyl; and $R_1$ is phenyl or substituted phenyl in which each substituent of said substituted phenyl, independently, is nitro or halo.

17. The composition of claim 16, wherein X is 3,5-dichlorophenyl; Y is —O—; and $R_1$ is 4-nitrophenyl and $R_2$ is H.

18. The composition of claim 16 wherein X is 3,5-dichlorophenyl; Y is —O—; and $R_1$ is 2-chloro-4-nitrophenyl and $R_2$ is H.

19. A method of treating cancer comprising administering to a patient in need thereof an effective amount of a compound of the formula:

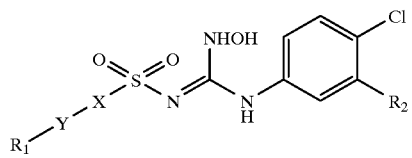

wherein

X is arylene, heteroarylene, fused arylene, fused heteroarylene, or deleted;

Y is sulfonyl, —O—, or deleted;

$R_1$ is aryl, heteroaryl, fused aryl, or fused heteroaryl; and $R_2$ is H, lower alkyl, lower alkoxy, halo, nitro, cyano, haloalkyl, hydroxyl, carboxyl, amido, amino, or aminoalkyl;

or a salt thereof.

20. The method of claim 19, wherein

X and Y are deleted; and $R_1$ is phenyl, substituted phenyl, benzothienyl, substituted benzothienyl, benzofuranyl, substituted benzofuranyl, benzothiadiazolyl, substituted benzothiadiazolyl, thienyl, substituted thienyl, in which each substituent of said substituted phenyl, substituted benzothienyl, substituted benzofuranyl, substituted benzothiadiazolyl, independently, is lower alkyl, lower alkoxy, halo, nitro, cyano, haloalkyl, hydroxyl, carboxyl, amido, amino, or aminoalkyl;

or a salt thereof.

21. The method of claim 19, wherein

X is phenylene, substituted phenylene, thienyl, or substituted thienyl in which each substituent of said substituted phenylene and substituted thienyl, independently, is lower alkyl, lower alkoxy, halo, nitro, cyano, haloalkyl, hydroxyl, carboxyl, amido, amino, or aminoalkyl; and $R_1$ is phenyl, substituted phenyl, benzothienyl, substituted benzothienyl, benzofuranyl, substituted benzofuranyl, benzothiadiazolyl, substituted benzothiadiazolyl, thienyl, substituted thienyl, in which each substituent of said substituted phenyl, substituted benzothienyl, substituted benzofuranyl, substituted benzothiadiazolyl, independently, is lower alkyl, lower alkoxy, halo, nitro, cyano, haloalkyl, hydroxyl, carboxyl, amido, amino, or aminoalkyl.

22. The method of claim 21, wherein

X is thienyl or substituted thienyl in which each substituent of said substituted thienyl, independently, is lower alkyl, lower alkoxy, halo, nitro, cyano, haloalkyl, hydroxyl, carboxyl, amido, amino, or aminoalkyl; and Y is sulfonyl or deleted.

23. The method of claim 21, wherein

X is phenylene or substituted phenylene in which each substituent of said substituted phenylene is, independently, lower alkyl, lower alkoxy, halo, nitro, cyano, haloalkyl, hydroxyl, carboxyl, amido, amino, or aminoalkyl; and Y is —O—.

24. The method of claim 23, wherein $R_2$ is H or halo.

25. The method of claim 24, wherein

X is phenylene or substituted phenylene in which each substituent of said substituted phenylene is, independently, halo, haloalkyl, nitro, amino, or aminoalkyl; and $R_1$ is phenyl or substitueted phenyl in which each substituent of substituted phenyl, independently, is nitro or halo.

26. The method of claim 25, wherein X is 3,5-dichlorophenyl; Y is —O—; and $R_1$ is 4-nitrophenyl and $R_2$ is H.

27. The method of claim 25, wherein X is 3,5-dichlorophenyl; Y is —O—; and $R_1$ is 2-chloro-4-nitrophenyl and $R_2$ is H.

* * * * *